United States Patent
Kumar (10) Patent No.: US 7,655,162 B2
(45) Date of Patent: Feb. 2, 2010

(54) ACETABULAR SHELL SYSTEM AND METHOD FOR MAKING

(75) Inventor: Mukesh Kumar, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 487 days.

(21) Appl. No.: 11/366,727

(22) Filed: Mar. 2, 2006

(65) Prior Publication Data
US 2006/0198943 A1    Sep. 7, 2006

Related U.S. Application Data

(60) Provisional application No. 60/658,407, filed on Mar. 3, 2005.

(51) Int. Cl.
A61F 2/34 (2006.01)
B29C 41/00 (2006.01)

(52) U.S. Cl. .................. 264/129; 606/76; 623/22.11

(58) Field of Classification Search ............. 264/129; 606/76; 623/22.11
See application file for complete search history.

(56) References Cited

U.S. PATENT DOCUMENTS

| | | | | |
|---|---|---|---|---|
| 3,429,962 A * | 2/1969 | Krystyniak | ............... | 264/309 |
| 3,855,638 A * | 12/1974 | Pilliar | ............... | 623/23.55 |
| 3,906,550 A * | 9/1975 | Rostoker et al. | ............ | 623/23.55 |
| 4,542,539 A | 9/1985 | Rowe, Jr. et al. | | |
| 4,612,160 A * | 9/1986 | Donlevy et al. | ............... | 419/2 |
| 4,715,860 A * | 12/1987 | Amstutz et al. | ............ | 623/22.33 |
| 4,854,496 A | 8/1989 | Bugle | | |
| 5,019,686 A * | 5/1991 | Marantz | ............... | 219/76.14 |
| 5,314,475 A | 5/1994 | Repenning | | |
| 5,366,669 A * | 11/1994 | Quadir et al. | ............... | 264/6 |
| 5,522,904 A * | 6/1996 | Moran et al. | ............. | 623/23.34 |
| 5,683,759 A * | 11/1997 | Shepard et al. | ............ | 427/569 |
| 5,807,407 A | 9/1998 | England et al. | | |
| 5,906,234 A * | 5/1999 | Mastrorio et al. | ............ | 164/45 |
| 6,008,432 A | 12/1999 | Taylor | | |
| 6,113,982 A * | 9/2000 | Claar et al. | ............... | 427/248.1 |
| 6,290,834 B1 | 9/2001 | Pearsall | | |
| 6,319,285 B1 | 11/2001 | Chamier et al. | | |
| 6,345,440 B1 | 2/2002 | Van Reatherford et al. | | |
| 6,491,967 B1 * | 12/2002 | Corderman et al. | ............ | 506/3 |
| 6,497,727 B1 * | 12/2002 | Pope et al. | ............... | 623/18.11 |
| 6,588,484 B1 | 7/2003 | Fosaaen et al. | | |
| 6,605,116 B2 * | 8/2003 | Falcon et al. | ............... | 623/8 |
| 6,827,742 B2 * | 12/2004 | Hayes et al. | ............ | 623/22.28 |
| 6,966,932 B1 * | 11/2005 | Schroeder | ............ | 623/22.19 |
| 2003/0050705 A1 | 3/2003 | Cueille et al. | | |
| 2004/0126599 A1 | 7/2004 | Wigren et al. | | |
| 2004/0152034 A1 | 8/2004 | Cummings et al. | | |

(Continued)

Primary Examiner—Joseph S. Del Sole
Assistant Examiner—John P Robitaille
(74) Attorney, Agent, or Firm—Harness, Dickey (57) ABSTRACT

A method for forming an acetabular shell includes providing a working surface such as a mandrel, and spraying the working surface with a first layer of material having a first composition such as aluminum oxide. After a suitable thickness is generated, the spray composition is gradually changed to other compositions having desired particle sizes and distribution. In one example, the composition is changed to a mixture of aluminum oxide and titanium oxide and/or titanium. As thickness builds up, the relative amount of aluminum oxide is decreased such that the composition is all titanium and titanium oxide. After a desired thickness is generated, the acetabular shell is extracted off the mandrel.

21 Claims, 5 Drawing Sheets

U.S. PATENT DOCUMENTS

2004/0243241 A1* 12/2004 Istephanous et al. ..... 623/17.14
2005/0085899 A1*  4/2005 Thornton ................... 623/1.16
2005/0119737 A1*  6/2005 Bene et al. ................... 623/4.1
2005/0158200 A1*  7/2005 Pope et al. .................... 419/11
2005/0267586 A1* 12/2005 Sidebotham ............. 623/22.41

* cited by examiner

ACETABULAR SHELL SYSTEM AND METHOD FOR MAKING

CROSS-REFERENCE TO RELATED APPLICATIONS

This application claims the benefit of a U.S. Provisional Application 60/658,407 filed on Mar. 3, 2005. The disclosure of the above application is incorporated herein by reference.

FIELD

This invention relates to acetabular shells and more particularly to a method of making an implant such as an acetabular shell by free form plasma (thermal) spray technology.

INTRODUCTION

In replacement hip surgery a femoral component can be inserted into the prepared femur. The femoral component can include a stem portion which projects into the femoral canal of the prepared femur and has an integral or separate modular head of substantially spherical shape. The ball-like head of the femoral component is received within an acetabular cup component which is implanted in the patient's hip socket, i.e., the acetabulum. The acetabular cup has a substantially hemispherical bearing surface for movement of the ball head of the femoral component during action of the joint.

Various designs of acetabular cups are available and it is often a multi-piece component having at least a separate outer shell and an inner liner. Where the acetabular cup has an inner liner, that inner liner is generally press-fitted into the outer shell. In some designs of hip prostheses the material of the bearing surface of the acetabular cup, e.g. its inner liner where present, is of the same material as that of the ball head, e.g. for a ceramic head, a ceramic bearing surface is provided (a so-called ceramic-on-ceramic prosthesis) and for a metal head, a metal bearing surface is provided (a so-called metal-on-metal prosthesis). In some other designs, the acetabular bearing surface is of polyethylene, as the acetabular cup is either provided with a polyethylene inner liner or the acetabular cup is a single component made entirely from polyethylene. The shape of the bearing surface into which the ball head is received affects the degree of movement available after implantation of the joint.

SUMMARY OF THE INVENTION

A method for forming an implant includes providing a working surface such as a mandrel, and spraying the working surface with a first layer of material having a first composition such as aluminum oxide. After a suitable thickness is generated, the spray composition is gradually changed to other compositions having desired particle sizes and distribution. In one example, the composition is changed to a mixture of aluminum oxide and titanium oxide and/or titanium. As thickness builds up, the relative amount of aluminum oxide is decreased such that the composition is all titanium and titanium oxide. After a desired thickness is generated, the acetabular shell is extracted off the mandrel.

A method of making an implant according to various features includes forming a ceramic shell having a first surface and a second surface. A first surface of the ceramic shell is located onto a mounting instrument. A layer of material is sprayed onto the second surface of the ceramic shell. The ceramic shell is then sintered.

Further areas of applicability of the present invention will become apparent from the detailed description provided hereinafter. It should be understood that the detailed description and specific examples, while indicating the embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the embodiment(s) is merely exemplary in nature and is in no way intended to limit the invention, its application, or uses. Moreover, while the description below is directed to an acetabular shell, the teachings described herein may similarly be employed to form other implants, such as, but not limited to femoral implants, tibial implants, tibial trays, and glenoid implants.

Figure 1:
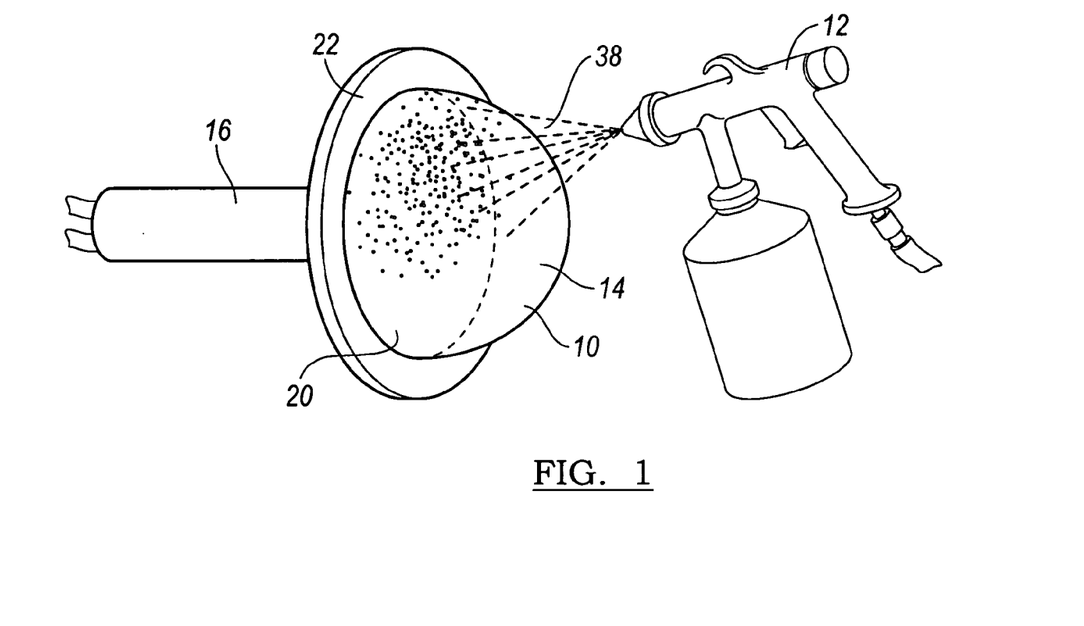
FIG. 1 illustrates an exemplary thermal spraying device spraying a first layer of material onto a mandrel.
Figure 2:
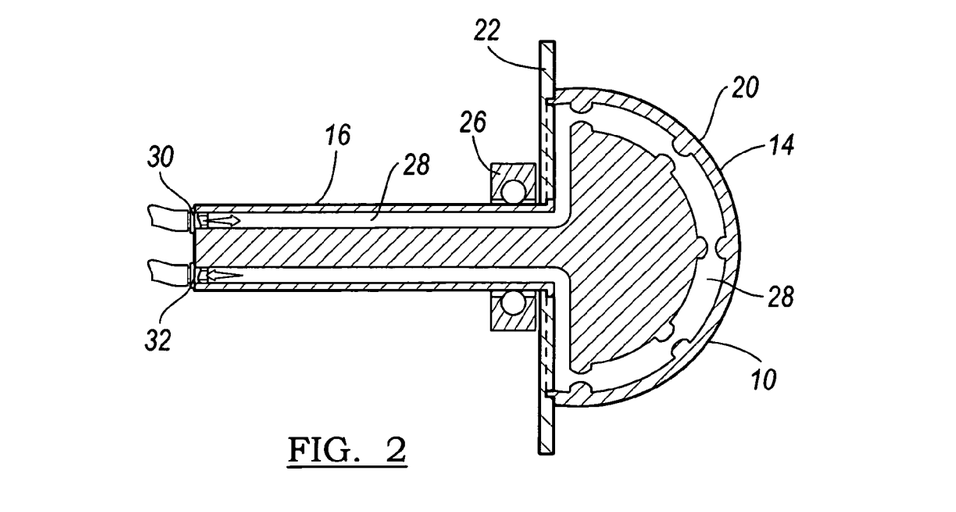
FIG. 2 illustrates a cross-sectional view of the mandrel of FIG. 1.

With initial reference now to FIGS. 1 and 2, a thermally stable mandrel and plasma spraying device are shown and identified at reference 10 and 12 respectively. The mandrel 10 generally defines a semi-hemispherical dome 14 and a longitudinal support portion 16. While the mandrel 10 and spraying device 12 are shown having specific geometries, it is appreciated that they are merely exemplary and other mandrels and spraying devices may be similarly employed.

The mandrel 10 is generally shaped inversely to a desired acetabular shell. More specifically, the mandrel 10 defines the semi-hemispherical dome 14 providing an outer convex surface 20 that corresponds to an inner concave surface of the acetabular shell. In one example, the thermally stable mandrel 10 may be made of tungsten. The outer convex surface 20 may be polished to a roughness acceptable for articulating surfaces of acetabular shells. The thermally stable mandrel 10 allows the generation of multiple acetabular shells without the need of individual grinding and polishing operations between subsequent shell formations.

With specific reference to FIG. 2, the mandrel 10 may be mounted on a holding fixture 22. The holding fixture 22 may provide a bearing set 26 for rotational capability. Other arrangements may also be provided.

The mandrel 10 may define a coolant channel 28 for communicating a coolant (not specifically shown) from an inlet 30 defined on the longitudinal portion 16 to an outlet 32 defined on the longitudinal portion 16. As shown, the coolant channel 28 is adapted to communicate fluid through the longitudinal portion 16, around the semi-hemispherical portion 14 and back through the longitudinal portion 16. The coolant port arrangement on the mandrel 10 helps draw away heat to maintain an acceptable temperature on the outer convex surface 20 and the mandrel 10 as a whole during a spray event. It is appreciated that the coolant channel 28 may be arranged differently on the mandrel 10 and/or other cooling mechanism or techniques may be employed to maintain acceptable mandrel temperatures during use. In one example, the mandrel 10 is maintained under 200° C. Other temperatures are contemplated. In addition, while not specifically shown, heat removal may be accomplished by flow of external gases over the acetabular shell being created.

Figure 3:
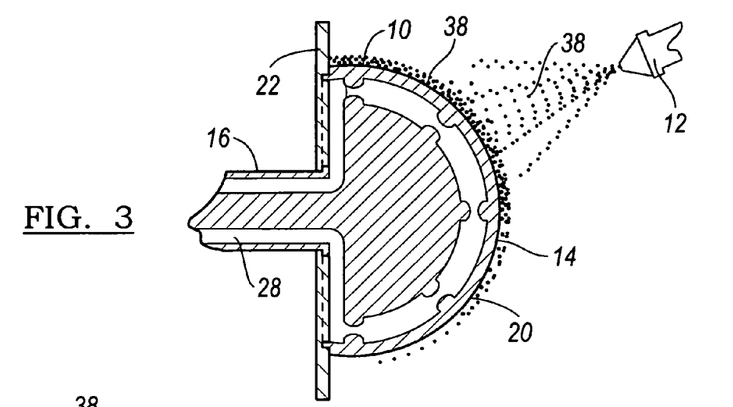
FIG. 3 illustrates a partial cross-sectional view of the spraying device and mandrel of FIG. 1 shown during an initial spraying step.

With continued reference to FIGS. 1 and 2 and additional reference to FIG. 3, a method of making an acetabular shell according to the present teachings will be described. In a controlled atmosphere, very fine powder of aluminum oxide 38 is sprayed onto the mandrel 10 such that a continuous layer of aluminum oxide 38 is generated on the mandrel 10 on the outer convex surface 20. The very fine powder exhausted from the spraying device 12 may be in the molten, or semi-molten state. In one example, prior to applying the aluminum oxide 38, a mold relief agent may be applied to the mandrel 12 to facilitate removal of the acetabular shell once completed.

Figure 4:
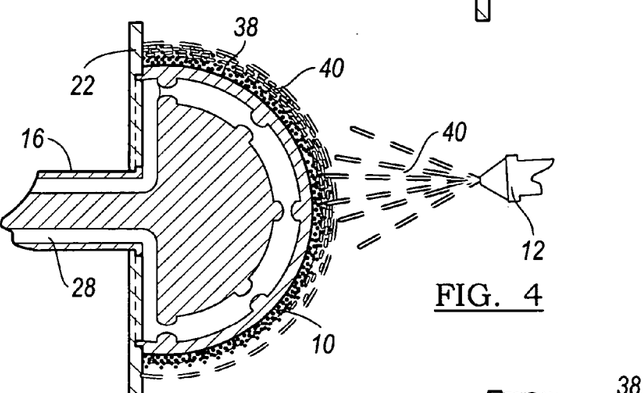
FIG. 4 illustrates the cross-sectional view of FIG. 3, shown during an intermediate spraying step.
Figure 5:
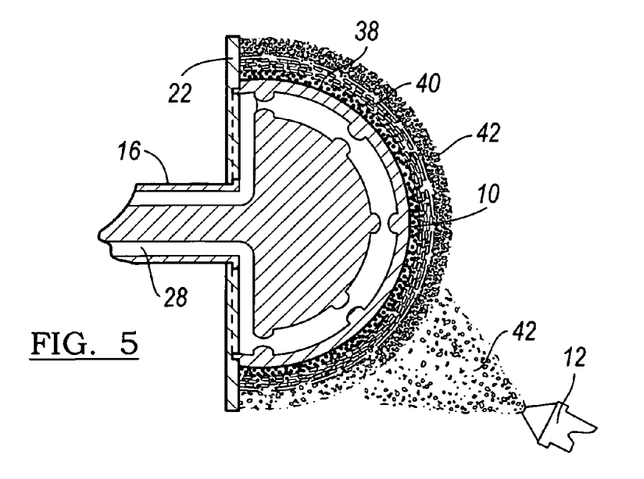
FIG. 5 illustrates the cross-sectional view of FIG. 4 shown during spraying of an outboard porous layer.

Once a suitable thickness (such as, but not limited to, less than 5 mm) of aluminum oxide 38 is sprayed onto the mandrel dome 14, the spray concentration changes to a mixture of aluminum oxide and titanium oxide and/or titanium collectively identified at reference 40 (FIG. 4). After a suitable thickness is generated (such as, but not limited to, 5 mm), the proportions of aluminum oxide is reduced causing the composition of titanium oxide and/or titanium to increase. This layer is identified at reference 42 (FIG. 5). The thickness of layer 42 may be 3 mm, although other thicknesses are contemplated.

Concurrently, the particle size of the titanium oxide and/or titanium may be increased to generate a porous outer surface. It is understood that while unique reference numerals 38, 40 and 42 have been used to identify sequential layers of sprayed material, the relative proportions of aluminum oxide, titanium oxide and/or titanium in the sprayed material gradually change as desired. As a result, there is not necessarily any identifiable transition boundaries across the thickness of the sprayed material.

Figure 6:
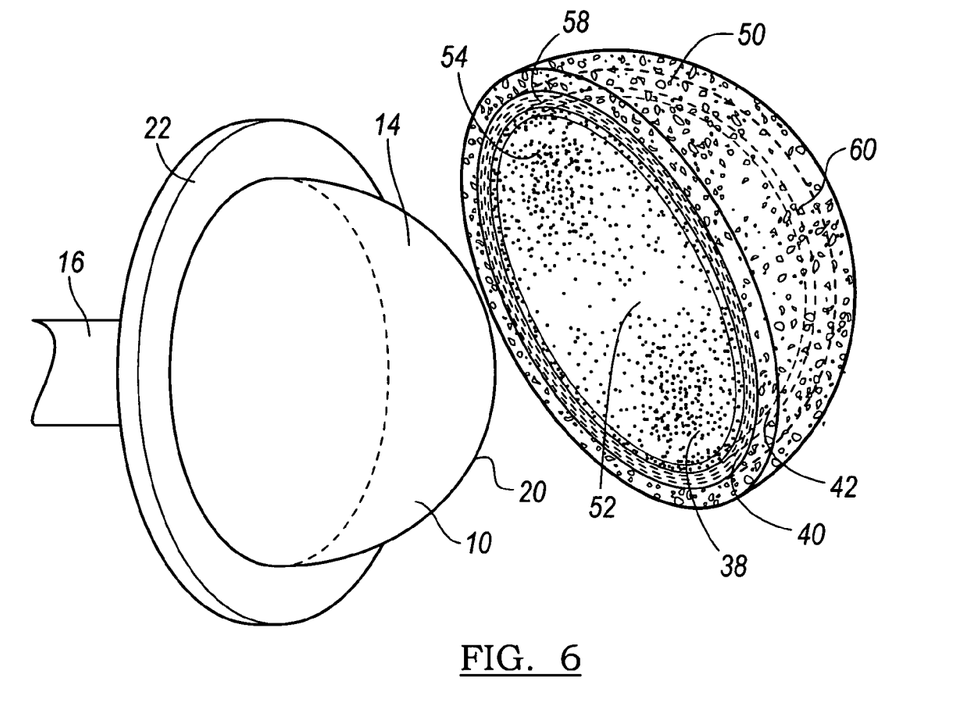
FIG. 6 illustrates the acetabular shell removed from the mandrel.
Figure 7:
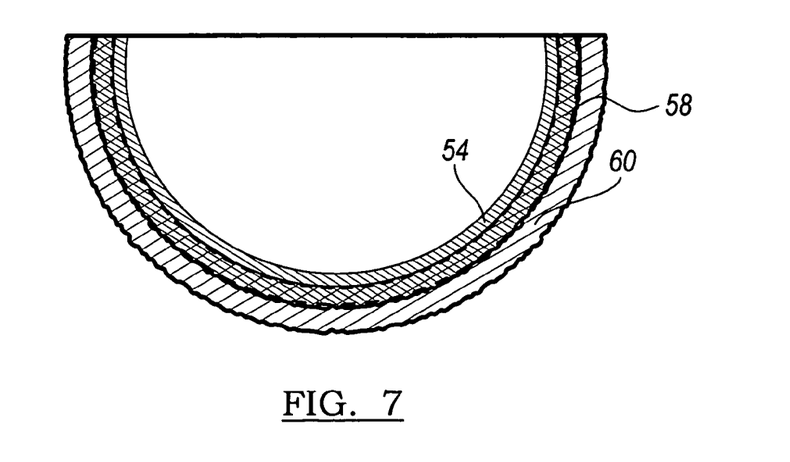
FIG. 7 illustrates a cross-sectional view of the acetabular shell of FIG. 6.

Turning now to FIG. 6, once a suitable thickness is achieved (such as, but not limited to, 13 mm), a newly formed acetabular shell 50 is extracted off the mandrel 10. The resulting acetabular shell 50 provides an inner portion 52 having a concave inner surface or articulating surface 54 of aluminum oxide, an intermediate portion 58 comprising a ceramic composition changing from aluminum oxide (from the articulating surface 54) to titanium and titanium oxide and finally to an outer portion 60 comprising porous titanium. The articulating surface of the acetabular shell 50 may then be polished to a desired roughness to serve as an articulating surface. It is appreciated that other materials may be used. For example, zirconia and/or other materials may be used for the aluminum oxide. Likewise, any composition of cobalt, chromium and/or molybdenum may be used for the titanium oxide and/or titanium. In addition, the acetabular shell may alternatively be made exclusively of one material.

In another embodiment, an implant such as a stem may take the place of the mandrel 10. As a result, the sequential layers may be sprayed directly onto the implant and remain on the implant as an integral feature.

Turning now to FIGS. 8-12, a method of making an acetabular shell according to an additional embodiment will be described. In this embodiment, rather than forming all layers of an acetabular shell by way of plasma spraying, a prefabricated ceramic shell 68 (FIG. 9) is used to define a template for receiving a subsequent plasma spray.

Figure 8:
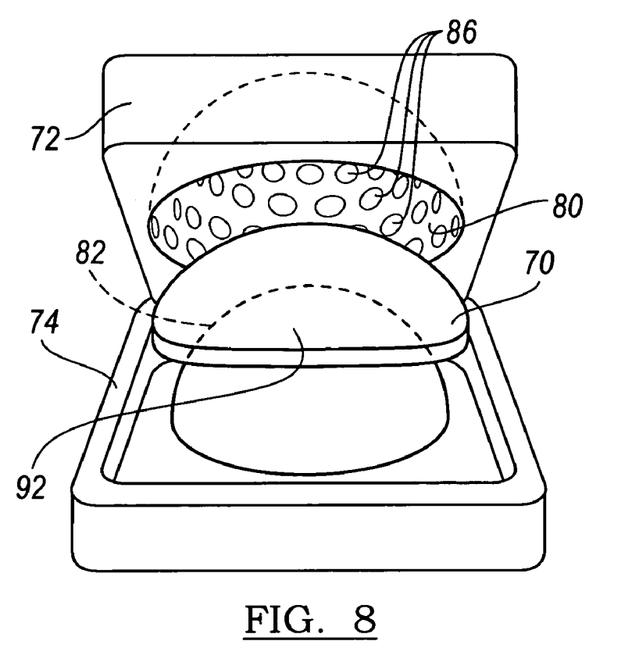
FIG. 8 illustrates a perspective view of a ceramic casting according to a another embodiment.
Figure 9:
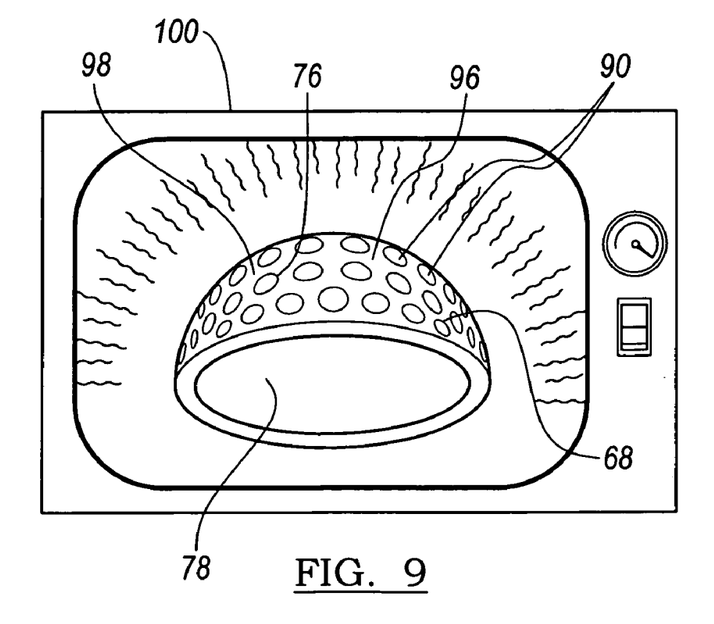
FIG. 9 illustrates a perspective view of a ceramic shell removed from the casting of FIG. 8.

As shown in FIG. 8, a ceramic shell 70 may be formed by way of a casting process. In one example, a first and second die 72 and 74 are used to define a desired outboard surface 76 and an inboard articulating surface 78 of the ceramic shell 70 (FIG. 9). As illustrated in FIG. 8, the first die 72 defines a concave cavity 80 and the second die 74 defines a convex extension surface 82. The concave cavity 80 defines a plurality of outward knobs 86. The outward knobs 86 are operable to define a textured surface, represented as dimples 90 on the outboard surface 76 of the cast ceramic shell 68 (FIG. 9). The convex extension surface 82 is operable to define the inboard articulating surface 78 of the cast ceramic shell 68. In one example, the walls of the concave cavity 80 are coated with titanium powder such that a layer of titanium is defined on outboard surface 76 of the cast ceramic shell 68.

During the casting process, a slurry of ceramic 92 is delivered to the first and second die 72 and 74. In one example, the slurry of ceramic 92 may be created in a fluid with binders and deflocculating agents as desired. The particle size of the ceramic, the quantity of binder and deflocculating agents and the ratio of various components in the slurry may be adjusted to achieve a slurry providing favorable casting properties. While the respective die cavities 72 and 74 are shown in an open position in FIG. 8, it is appreciated that the slurry of ceramic 92 may be delivered through a port to a closed die cavity.

As shown in FIG. 9, the ceramic shell 68 defines a hemispherical dome 96. It is appreciated that other shapes may be alternatively formed. It is further appreciated that while the textured surface is depicted as dimples 90, the first die 72 may be configured to define any textured surface including, but not limited to, ridges, notches and other configurations. Furthermore, while the formation of the ceramic shell 68 has been described by way of a casting process, other fabrication techniques may be used. Once the ceramic shell 68 has been cast, the ceramic shell 68 is dried or semi-dried into a stable dome 98. In one example, the process of converting the ceramic shell 68 to a semi-dried, stable dome 98 may be achieved in a baking oven 100. The baking oven 100 is operable to drive off any excess fluid slurry. Furthermore, any binders and/or deflocculating agents may or may not be removed.

Figure 10:
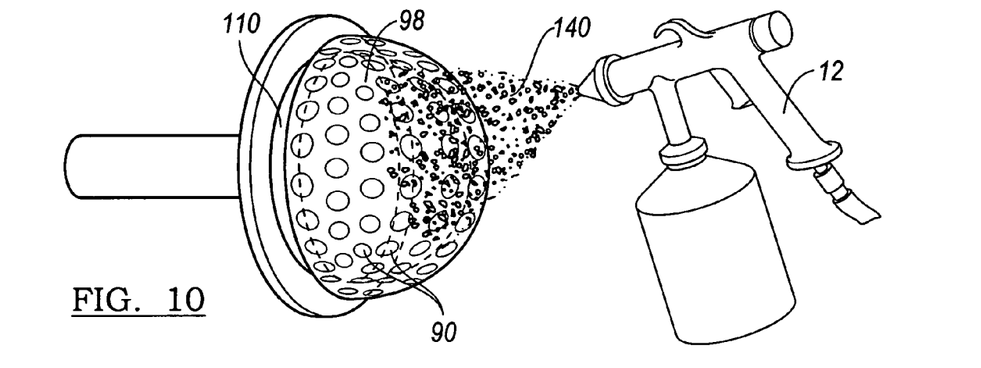
FIG. 10 illustrates a perspective view of the ceramic shell arranged on a mandrel and a spraying device spraying a layer of material onto an outer concave surface of the ceramic shell.

Turning now to FIG. 10, the stable dome 98 may be placed onto a mandrel 110. The mandrel 110 may cooperate with a longitudinal support portion 116, a holding fixture 122 and a bearing set 126. Furthermore, the mandrel 110 may include a coolant channel 128. Again, other configurations may be employed.

Figure 11:
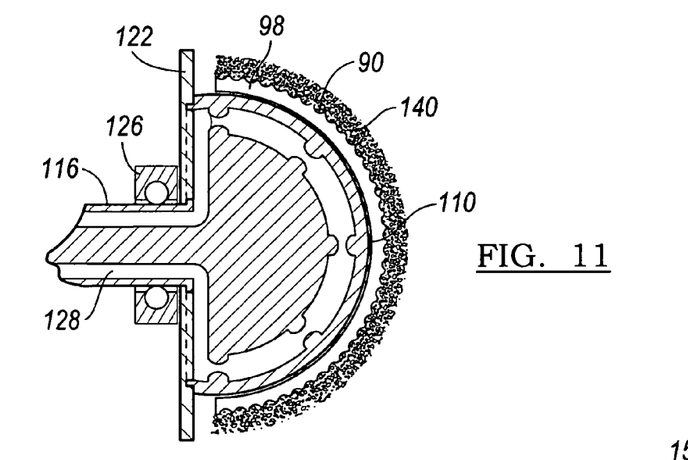
FIG. 11 illustrates a cross-sectional view of the ceramic shell having the layer of material sprayed thereon and defining an acetabular shell.

Next, a layer of titanium oxide 140 is sprayed with a plasma sprayer 12 to a desired thickness. As best illustrated in FIG. 11, mechanical interlocking is achieved between the titanium oxide 140 and the outboard textured surface 90 of the ceramic dome 98. The interface between the textured surface 90 and the titanium oxide 140 resists torsional slippage and radial slippage of the titanium oxide 140 relative the outboard surface 76 of the ceramic dome 98.

Figure 12:
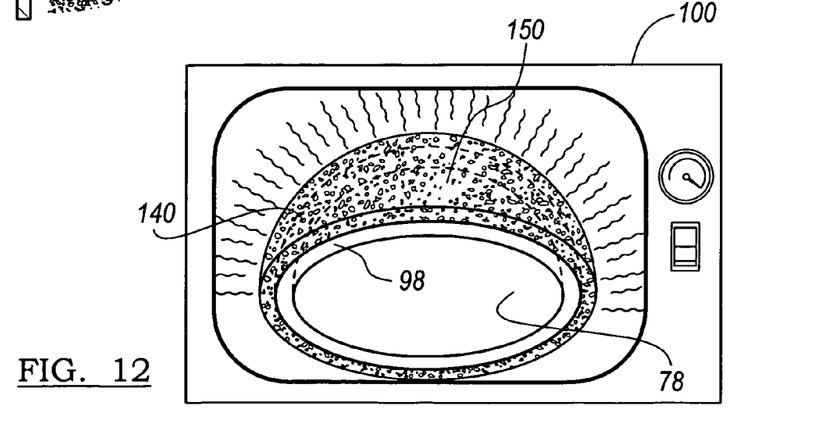
FIG. 12 illustrates the acetabular shell of FIG. 11 shown during a sintering process.

With reference now to FIG. 12, a newly formed acetabular shell 150 is then placed into a baking oven 100 for a sintering process. In one example, a sinter cycle may be performed as follows. First, the oven temperature may be raised to 175° C. at 5° C./min. The 175° C. may be maintained for 4 hours. The temperature may be ramped to a peak temperature such as 1650° C. at 5° C./min (optionally lower temperatures may be used i.e. 1300° C.-1450° C.). The peak temperature may be maintained for 8 hours. It is appreciated that a peak temperature of 130° C.-1450° C. may be maintained for longer periods than higher temperatures (such as 1650° C.). The temperature may be ramped down to 600° C. at 5° C./min. The 600° C. temperature may be held for 30 minutes.

It is appreciated that the sintering procedure explained above is merely exemplary. As such, ramp rate, dwell time and dwell temperatures (collectively referred to as variables) of the sinter cycle may define other ranges. The variable assigned during the sinter process may be chosen to discourage crack formation in the structure. In one example, a thermally induced compressive stress may be generated in the ceramic structure to discourage premature failure.

Once the acetabular shell 150 is sintered, the concave inner surface 78 may be polished to a desired roughness to serve as an articulating surface.

While the invention has been described in the specification and illustrated in the drawings with reference to various embodiments, it will be understood by those skilled in the art that various changes may be made and equivalents may be substituted for elements thereof without departing from the scope of the invention as defined in the claims. Furthermore, the mixing and matching of features, elements and/or functions between various embodiments is expressly contemplated herein so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the foregoing description and the appended claims.

What is claimed is:

1. A method for forming an acetabular cup for use in replacing a portion of a patient's hip, the method comprising:
   providing a working surface onto which an acetabular cup is to be formed;
   spraying a first layer of material having a first composition onto the working surface, the first layer of material forming a concave inner bearing engaging surface of the acetabular cup;
   continuing the spraying of the first material while introducing a second material having a second composition into the spray such that a concentration of the first and second materials are sprayed together to form a mixture of the first and second materials as a second layer of material subsequent to spraying the first layer of material;
   continuing the spraying while reducing an amount of the first material in the concentration, such that a third layer of material consisting solely of the second material is formed, the third layer of material having an outermost surface forming a convex outer bone engaging surface of the acetabular cup capable of engaging the portion of the patient's hip, the first, second and third layers of material collectively forming the acetabular cup; and
   removing the acetabular cup from the working surface.

2. The method of claim 1 wherein the working surface comprises a mandrel having an outer convex surface, and wherein spraying the first layer includes spraying the frst layer on the outer convex surface.

3. The method of claim 2, further comprising passing coolant through a coolant channel defined in the mandrel.

4. The method of claim 3 wherein the mandrel is formed from tungsten.

5. The method of claim 1 wherein providing the working surface further comprises spraying a mold relief agent onto the working surface.

6. The method of claim 1 wherein spraying the first layer of material comprises spraying a continuous layer of aluminum oxide.

7. The method of claim 6 wherein spraying the second layer of material comprises spraying a first mixture comprising aluminum oxide and at least one of titanium and titanium oxide.

8. The method of claim 7 wherein spraying the third layer of material further comprises spraying an outboard layer of titanium onto the bone engaging surface.

9. The method of claim 8 wherein spraying the first and second layers of material comprises plasma spraying the first and second layers of material.

10. The method of claim 2, further comprising polishing an articulating surface defined on the inner bearing engaging surface of the first layer of material.

11. A method of forming an implant for use in replacing a portion of a patient's joint, the method comprising:
    providing a mandrel having a semi-hemispherical dome and including an outer convex working surface;
    spraying a first material onto the outer convex working surface forming a concave inner bearing engaging surface of the implant on an innermost surface of the first material;
    subsequently spraying a combination of the first material and a second material forming a mixture of the first and second materials as an intermediate layer of the implant;
    subsequently discontinuing spraying of the first material while continuing to spray the second material onto the intermediate layer forming a convex bone engaging surface of the implant on an outermost surface of the second material;
    concluding the spraying thereby forming an implant having the concave bearing engaging surface formed of the first material and the convex bone engaging surface capable of engaging the portion of the patient's joint and being formed of the second material, the first and second materials being distinct; and
    removing the implant from the working surface.

12. The method of claim 11, wherein subsequently discontinuing spraying of the first material further comprises progressively reducing an amount of the first material in the concentration.

13. The method of claim 11, further comprising passing coolant through a coolant channel defined in the mandrel.

14. The method of claim 13 wherein the mandrel is formed from tungsten.

15. The method of claim 11 further comprising spraying a mold relief agent onto the outer convex working surface.

16. The method of claim 12 wherein spraying the first material comprises spraying a continuous layer of aluminum oxide.

17. The method of claim 16 wherein spraying the second material comprises spraying a first mixture comprising aluminum oxide and at least one of titanium and titanium oxide.

18. The method of claim 17 wherein spraying the second material further comprises plasma spraying an outboard layer of titanium onto the intermediate layer.

19. The method of claim 18 wherein spraying the first and second material comprises plasma spraying the first and second material.

20. The method of claim 11, further comprising polishing an articulating surface defined on the first material.

21. The method of claim 11 wherein the implant comprises an acetabular shell.

* * * * *

UNITED STATES PATENT AND TRADEMARK OFFICE
CERTIFICATE OF CORRECTION

| | | |
|---|---|---|
| PATENT NO. | : 7,655,162 B2 | |
| APPLICATION NO. | : 11/366727 | |
| DATED | : February 2, 2010 | |
| INVENTOR(S) | : Kumar | |

It is certified that error appears in the above-identified patent and that said Letters Patent is hereby corrected as shown below:

Col. 5, line 13, delete "130°" and replace with "1300°".

Signed and Sealed this

Sixth Day of April, 2010

David J. Kappos
*Director of the United States Patent and Trademark Office*